United States Patent
Akinc et al.

(10) Patent No.: US 8,324,366 B2
(45) Date of Patent: Dec. 4, 2012

(54) COMPOSITIONS AND METHODS FOR DELIVERING RNAI USING LIPOPROTEINS

(75) Inventors: Akin Akinc, Needham, MA (US); Tomoko Nakayama, Cambridge, MA (US); Muthiah Manoharan, Weston, MA (US); Markus Stoffel, New York, NY (US)

(73) Assignees: Alnylam Pharmaceuticals, Inc., Cambridge, MA (US); Eth Zurich, Zurich (CH)

(*) Notice: Subject to any disclaimer, the term of this patent is extended or adjusted under 35 U.S.C. 154(b) by 34 days.

(21) Appl. No.: 12/432,192

(22) Filed: Apr. 29, 2009

(65) Prior Publication Data

US 2009/0286851 A1  Nov. 19, 2009

Related U.S. Application Data

(60) Provisional application No. 61/048,922, filed on Apr. 29, 2008.

(51) Int. Cl.
*C07H 21/02* (2006.01)
*C07H 21/04* (2006.01)

(52) U.S. Cl. ............ 536/24.5; 536/23.1; 536/24.3; 536/24.33

(58) Field of Classification Search ............ 536/23.1, 536/24.3, 24.33, 24.5; 514/44
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 4,587,044 A | 5/1986 | Miller et al. | |
| 4,605,735 A | 8/1986 | Miyoshi et al. | |
| 4,643,988 A | 2/1987 | Segrest et al. | |
| 4,667,025 A | 5/1987 | Miyoshi et al. | |
| 4,762,779 A | 8/1988 | Snitman | |
| 4,789,737 A | 12/1988 | Miyoshi et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,876,335 A | 10/1989 | Yamane et al. | |
| 4,904,582 A | 2/1990 | Tullis | |
| 4,948,882 A | 8/1990 | Ruth | |
| 4,958,013 A | 9/1990 | Letsinger | |
| 5,013,556 A | 5/1991 | Woodle et al. | |
| 5,032,401 A | 7/1991 | Jamas et al. | |
| 5,082,830 A | 1/1992 | Brakel et al. | |
| 5,109,124 A | 4/1992 | Ramachandran et al. | |
| 5,112,963 A | 5/1992 | Pieles et al. | |
| 5,118,802 A | 6/1992 | Smith et al. | |

(Continued)

FOREIGN PATENT DOCUMENTS

CA  2138925  1/1995

(Continued)

OTHER PUBLICATIONS de Smidt et al. (Nucleic Acids Research, 1991 vol. 19., No. 17:4695-4709).*

(Continued)

*Primary Examiner* — Terra Cotta Gibbs
(74) *Attorney, Agent, or Firm* — Lando & Anastasi, LLP

(57) ABSTRACT

This invention relates to new compositions comprising at least one of a single or double stranded oligonucleotide, where said oligonucleotide has been conjugated to a lipophile and to which the conjugated oligonucleotide has been preassembled with lipoproteins. These compositions are effectively in delivering oligonucleotides to mammalian tissue where they effect gene silencing.

18 Claims, 6 Drawing Sheets

U.S. PATENT DOCUMENTS

| | | | |
|---|---|---|---|
| 5,128,318 | A | 7/1992 | Levine et al. |
| 5,138,045 | A | 8/1992 | Cook et al. |
| 5,213,804 | A | 5/1993 | Martin et al. |
| 5,214,136 | A | 5/1993 | Lin et al. |
| 5,218,105 | A | 6/1993 | Cook et al. |
| 5,225,212 | A | 7/1993 | Martin et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,272,250 | A | 12/1993 | Spielvogel et al. |
| 5,292,873 | A | 3/1994 | Rokita et al. |
| 5,317,098 | A | 5/1994 | Shizuya et al. |
| 5,356,633 | A | 10/1994 | Woodle et al. |
| 5,371,241 | A | 12/1994 | Brush |
| 5,391,723 | A | 2/1995 | Priest |
| 5,414,077 | A | 5/1995 | Lin et al. |
| 5,416,203 | A | 5/1995 | Letsinger |
| 5,451,463 | A | 9/1995 | Nelson et al. |
| 5,486,603 | A | 1/1996 | Buhr |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,525,465 | A | 6/1996 | Haralambidis et al. |
| 5,525,472 | A | 6/1996 | Lifshitz et al. |
| 5,540,935 | A | 7/1996 | Miyazaki et al. |
| 5,541,313 | A | 7/1996 | Ruth |
| 5,545,730 | A | 8/1996 | Urdea et al. |
| 5,552,538 | A | 9/1996 | Urdea et al. |
| 5,556,948 | A | 9/1996 | Tagawa et al. |
| 5,565,552 | A | 10/1996 | Magda et al. |
| 5,567,810 | A | 10/1996 | Weis et al. |
| 5,574,142 | A | 11/1996 | Meyer, Jr. et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,371 | A | 12/1996 | Sessler et al. |
| 5,591,584 | A | 1/1997 | Chang et al. |
| 5,595,726 | A | 1/1997 | Magda et al. |
| 5,597,696 | A | 1/1997 | Linn et al. |
| 5,599,923 | A | 2/1997 | Sessler et al. |
| 5,599,928 | A | 2/1997 | Hemmi et al. |
| 5,607,677 | A | 3/1997 | Jamas et al. |
| 5,608,046 | A | 3/1997 | Cook et al. |
| 5,688,941 | A | 11/1997 | Cook et al. |
| 6,747,014 | B2 | 6/2004 | Teng et al. |
| 6,887,906 | B1 | 5/2005 | Teng et al. |
| 2003/0027780 | A1 | 2/2003 | Hardee et al. |
| 2003/0143732 | A1 | 7/2003 | Fosnaugh et al. |
| 2004/0214325 | A1 | 10/2004 | Crooke et al. |
| 2004/0229831 | A1 | 11/2004 | Teng et al. |
| 2004/0259247 | A1 | 12/2004 | Tuschl et al. |
| 2005/0281781 | A1 | 12/2005 | Ostroff |
| 2006/0189561 | A1 | 8/2006 | Roelvink et al. |
| 2007/0004664 | A1 | 1/2007 | McSwiggen et al. |
| 2007/0031844 | A1 | 2/2007 | Khvorova et al. |
| 2008/0160094 | A1 | 7/2008 | Nelson et al. |

FOREIGN PATENT DOCUMENTS

| | | |
|---|---|---|
| EP | 0329605 B1 | 8/1989 |
| EP | 0353267 A1 | 2/1990 |
| EP | 0445131 B1 | 4/1994 |
| EP | 0496813 B1 | 12/1994 |
| WO | WO 87/02062 | 4/1987 |
| WO | WO 90/04384 | 5/1990 |
| WO | WO 91/05545 | 5/1991 |
| WO | WO 92/05571 | 4/1992 |
| WO | WO 94/20073 | 9/1994 |
| WO | WO 96/10391 | 4/1996 |

OTHER PUBLICATIONS

Matsuo et al. (Atherosclerosis, 2007 vol. 194:159-168, available online Nov. 21, 2006).*

Hammond et al. (Nature Reviews Genetics 2001, vol. 2:110-119).*

Rensen et al. (Advanced Drug Delivery Reviews, 2001 vol. 47:251-276).*

Jonas, A., "A review of plasma apolipoprotein A-I interactions with phosphatidylcholines," Experimental Lung Res., 1984, vol. 6, Issue 3 &4, pp. 255-270.

Jonas, A., "Reconstitution of High-Density Lipoproteins," Methods in Enzymology, 1986, pp. 553-582, vol. 128.

Franceschini, G., et al., "Accelerated Binding and Dissociation From Lipids of a Human Apolipoprotein," J. Biol. Chem., 1985, vol. 260 (30), pp. 16231-25.

Block, L., "Emulsions and Microemulsions," Pharmaceutical Dosage Forms, Chapter 9, Lieberman, Rieger and Banker (Eds.), 1988, Marcel Dekker, Inc., New York, N.Y., vol. 2, p. 335-378.

Idson, B., "Pharmaceutical Emulsions," Pharmaceutical Dosage Forms, Chapter 6, Lieberman, Rieger and Banker (Eds.), 1988, Marcel Dekker, Inc., New York, N.Y., vol. 1, p. 199-243.

Higuchi et al., in Remington's Pharmaceutical Sciences, "Particle Phenomena and Coarse Dispersions," Chapter 21, Mack Publishing Co., Easton, Pa., 1985, p. 301-329.

Leung, R., et al., "Controlled Release of Drugs: Polymers and Aggregate Systems," Chapter 6, Microemulsions: An Evolving Technology for Pharmaceutical Applications, Rosoff, M., Ed., 1989, VCH Publishers, New York, pp. 185-215.

Rosoff, M., "Specialized Pharmaceutical Emulsions," Pharmaceutical Dosage Forms, Chapter 7, Lieberman, Rieger and Banker (Eds.), 1988, Marcel Dekker, Inc., New York, N.Y., vol. 1, p. 245-283.

Allen, T.M., et al., "Large unilamellar liposomes with low uptake into the reticuloendothelial system," FEBS Letters, Oct. 1987, vol. 223, No. 1, pp. 42-46.

Blume, G., et al., "Liposomes for the sustained drug release in vivo," Biochimica et Biophysica Acta, 1990, vol. 1029, pp. 91-97.

Bonomo, E. A., et al., "A rapid method for the synthesis of protein-lipid complexes using adsorption chromatography," J. Lipid Res., 1988, vol. 29, pp. 380-384.

Du Plessis, J., et al., "Research Articles Topical delivery of liposomally encapsulated gamma-interferon," Antiviral Research, 1992, vol. 18, pp. 259-265.

Constantinides P., et al., "Formulation and Intestinal Absorption Enhancement Evaluation of Water-in-Oil Microemulsions Incorporating Medium-Chain Glycerides," Pharmaceutical Research, 1994, vol. 11, No. 10, 1385-1390.

Ho, H., et al., "Preparation of Microemulsions Using Polyglycerol Fatty Acid Esters as Surfactant for the Delivery of Protein Drugs," J. Pharm. Sci., Feb. 1996, vol. 85, No. 2, pp. 138-143.

Hu, Z., et al., "Topical delivery of cyclosporin A from non-ionic liposomal systems: an in vivo/in vitro correlation study using hairless mouse skin," S.T.P.Pharma. Sci., 1994, vol. 4, No. 6, pp. 466-469.

Lee, V., et al., "Mucosal Penetration Enhancers for Facilitation of Peptide and Protein Drug Absorption," Critical Reviews in Therapeutic Drug Carrier Systems, 1991, vol. 8, No. 2, pp. 91-192.

Illum, L., et al., "The organ uptake of intravenously administered colloidal particles can be altered using a non-ionic surfactant (Poloxamer 338)," FEBS Lett., Feb. 1984, vol. 167, No. 1, pp. 79-82.

Klibanov, A., et al., "Amphipathic polyethyleneglycols effectively prolong the circulation time of liposomes," FEBS Lett., Jul. 1990, vol. 268, No. 1, pp. 235-237.

Miyao, T., et al., "Stability and Pharmacokinetic Characteristics of Oligonucleotides Modified at Terminal Linkages in Mice," Antisense Research and Dev., 1995, vol. 5, pp. 115-121.

Ritschel, W.A., "Microemulsions for Improved Peptide Absorption from the Gastointestinal Tract," Meth. Find. Exp. Clin. Pharmacol., 1993, vol. 13, No. 3, pp. 205-220.

Sunamoto, J., et al., "Liposomal Membranes. V. Interaction of Zinc (II) Ion with Egg Phosphatidylcholine Liposomes," Bull. Chem. Soc. Jpn., 1980, vol. 53, No. 10, pp. 2778-2781.

Takakura, Y., et al., "Uptake Characteristics of Oligonucleotides in the Isolated Rat Liver Perfusion System," Antisense & Nucl. Acid Drug Dev., 1996, vol. 6, pp. 177-183.

Torchilin, V. P., "Recent advances with liposomes as pharmaceutical carriers," Nature Rev. Drug Discov., Feb. 2005, vol. 4, No. 2, pp. 145-160.

Weiner, N., et al., "Liposomes: A Novel Topical Delivery System for Pharmaceutical and Cosmetic Applications," Journal of Drug Targeting, 1992, vol. 2, pp. 405-410.

Wolfrum, et al., "Mechanisms and optimization of in vivo delivery of lipophilic siRNAs," Nature Biotechnology, Oct. 2007, vol. 25, No. 10, pp. 1149-1157.

Wu, N., et al., "Increased Microvascular Permeability Contributes to Preferential Accumulation of Stealth Lipisomes in Tumor Tissue," Cancer Research, Aug. 15, 1993, vol. 53, pp. 3765-3770.

Agrawal, S., et al., "Antisense oligonucleotides: towards clinical trials." Trends in Biotechnology. Oct. 1996, vol. 14, pp. 376-387.

Bass, B., "The short answer," Nature, May 24, 2001, pp. 428-429, vol. 411.

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.

Elbashir, S., et al., "RNA Interference is Mediated by 21-and 22 Nucleotide RNAs," Genes & Development, 2001, pp. 188-200, vol. 15.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA in Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

\* cited by examiner (a)

(b)

(C)

(d)

(a)

(b)

SEQUENCE LISTING

<160> NUMBER OF SEQ ID NOS: 13

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gucaucacac ugaauaccaa u                                            21

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
auugguauuc agugugauga cac                                          23

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
agucaaucgg uauguccact t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
guggacauac cgauugacut t                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
agucagucag uguauccact t                                            21

<210> SEQ ID NO 6

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
guggauacac ugacugacut t                                                  21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagcaactg atatttgta                                                     19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agctggtcat tacctatca                                                     19

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcctgttgc agtagagtgc agct                                               24

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctctagagcg actggagcac gaggacacta                                         30

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgcgtcgac gtgggagcat ggaggttggc agttgttc                                38
```

```
<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaaucuuau auuugaucca a                                              21

<210> SEQ ID NO 13
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uuggaucaaa uauaagauuc ccu                                            23
```

COMPOSITIONS AND METHODS FOR DELIVERING RNAI USING LIPOPROTEINS

CROSS-REFERENCE TO RELATED APPLICATIONS

This application claims priority to U.S. Application Ser. No. 61/048,922, filed Apr. 29, 2008. The entire contents of this provisional application is hereby incorporated by reference in the present application.

FIELD OF THE INVENTION

This invention relates to the use of lipoproteins with oligonucleotides, both single and double stranded and their use in delivering RNA interference. More specifically, the present invention relates to compositions containing oligonucleotides and lipoproteins which enable tissue-specific delivery and reduction of target expression.

BACKGROUND OF THE INVENTION

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in C. elegans. dsRNA has also been shown to degrade target RNA in other organisms, including plants (see, e.g., WO 99/53050, Waterhouse et al.; and WO 99/61631, Heifetz et al.), Drosophila (see, e.g., Yang, D., et al., Curr. Biol. (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pathological processes, there remains a need for formulations that can selectively and efficiently deliver agents to cells where silencing can then occur.

While delivery of oligonucleotides across plasma membranes in vivo has been achieved using vector-based delivery systems, high-pressure intravenous injections of oligonucleotides and various chemically-modified oligonucleotides, including cholesterol-conjugated, lipid encapsulated and antibody-mediated oligonucleotides, to date, delivery remains the largest obstacle for in vivo oligonucleotide therapeutics.

SUMMARY OF THE INVENTION

The invention provides compositions containing oligonucleotides and methods for inhibiting the expression of a gene in a cell or mammal using such oligonucleotides in combination with lipoproteins. The invention also provides compositions and methods for treating pathological conditions and diseases caused by the expression of a target gene, such as cancer. The oligonucleotides of the invention which are double stranded included in the compositions featured herein include double-stranded RNA (dsRNA) having an RNA strand (the antisense strand) having a region which is less than 30 nucleotides in length, generally 18-30 nucleotides in length, and is substantially complementary to at least part of an mRNA transcript of the target gene. In one embodiment, a dsRNA for inhibiting expression of the target gene includes at least two sequences that are complementary to each other. The dsRNA includes a sense strand having a first sequence and an antisense strand having a second sequence. The antisense strand includes a nucleotide sequence that is substantially complementary to at least part of an mRNA encoding target gene, and the region of complementarity is less than 30 nucleotides in length, and at least 18 nucleotides in length. Generally, the dsRNA is 18 to 30, e.g., 19 to 21 nucleotides in length. In one embodiment the strands are independently 18-30 nucleotides.

In like fashion the single-stranded oligonucleotides of the present invention also comprise nucleotide sequence that is substantially complementary to at least part of an mRNA encoding target gene, and the region of complementarity is less than 30 nucleotides in length, and at least 15 nucleotides in length. Generally, the single stranded oligonucleotides are 18 to 30, e.g., 19 to 21 nucleotides in length. In one embodiment the strand is 18-30 nucleotides. Single strands having less than 100% complementarity to the target mRNA, RNA or DNA are also embraced by the present invention.

The oligonucleotides featured herein can include naturally occurring nucleotides or can include at least one modified nucleotide, such as a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

The oligonucleotides of the present invention may be preferably stabilized by one or more modifications to avoid degradation of the oligonucleotides. Possible modifications are phosphorothioate units, 2'-O-methyl RNA units, 2'-O-methoxy-ethyl RNA units, peptide nucleic acid units, N3'-P5' phosphoroamidate DNA units, 2' fluoro-ribo nucleic acid units, Locked nucleic acid units, morpholino phosphoroamidate nucleic acid units, cyclohexane nucleic acid units, tricyclonucleic acid units, 2'-O-alkylated nucleotide modifications, 2'-Deozy-2'-fluoro modifications, 2,4-difluorotoluoyl modifications, 4'-thio ribose modifications, or boranophospate modifications.

In one embodiment, the oligonucleotides of the present invention are preassembled with lipoproteins. It has been surprisingly discovered that when oligonucleotides, either single- or double stranded, are preassembled with high density lipoproteins, both delivery and silencing are effected in tissues in vivo, particularly liver.

In another embodiment, the invention provides a pharmaceutical composition for inhibiting the expression of the target gene in an organism, generally a human subject. The composition typically includes one or more of the dsRNAs described herein and a pharmaceutically acceptable carrier or delivery vehicle.

In another embodiment, the invention provides methods for treating, preventing or managing pathological processes mediated by a target gene by administering to a patient in need of such treatment, prevention or management a therapeutically or prophylactically effective amount of one or more of the compositions of the invention.

DETAILED DESCRIPTION OF THE INVENTION

Figure 1:
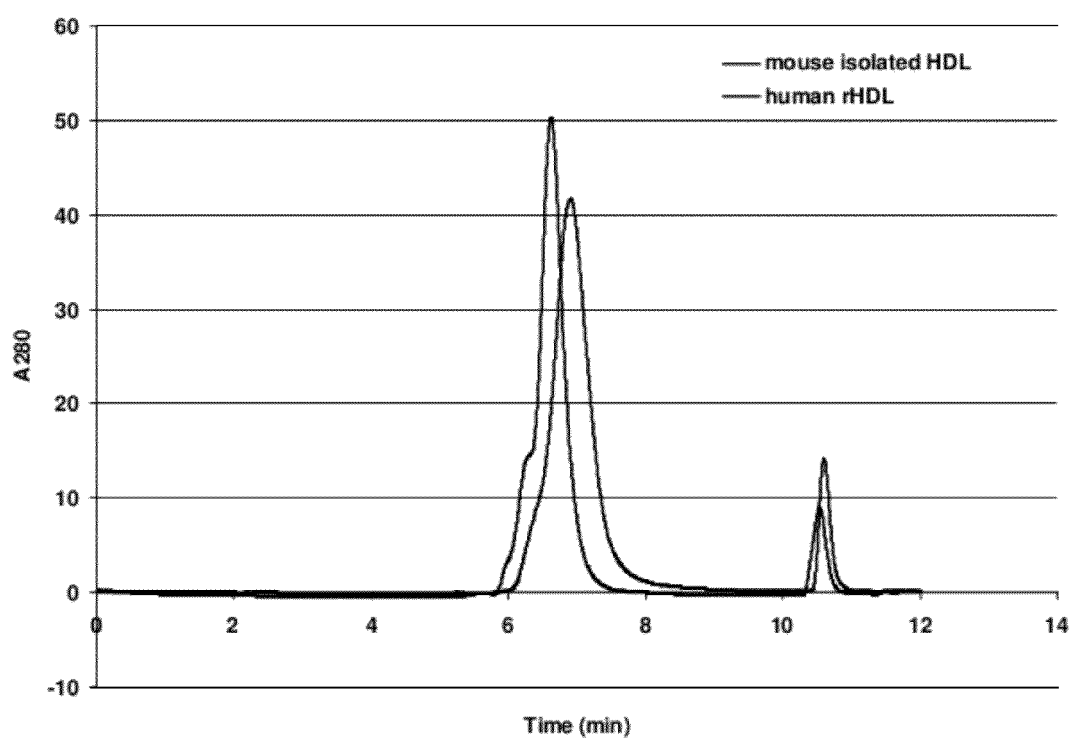
FIG. 1 illustrates a comparison of isolated and reconstituted HDL by SEC HPLC. rHDL appears only slightly larger than isolated mouse HDL; x axis is Time (min) and y axis is A280.

The invention provides compositions and methods for inhibiting the expression of a target gene in a cell or mammal using single- and/or double-stranded oligonucleotides. The oligonucleotides are preferably conjugated to one or more lipophiles and preassembled with lipoproteins. This invention is based on the discovered that when lipophilic conjugated oligonucleotides, either single- or double stranded, are preassembled with lipoproteins, both delivery and silencing are effected in tissues in vivo, particularly liver tissue.

A composition comprises (a) at least one of a single or double stranded oligonucleotide, where said oligonucleotide has been conjugated to a lipophile and (b) lipoproteins.

The invention also provides compositions and methods for treating pathological conditions and diseases, such as cancer, in a mammal caused by the overexpression of the target gene. The oligonucleotide component, whether single stranded or double stranded directs the sequence-specific degradation of mRNA through the antisense mechanism known as RNA interference (RNAi).

The oligonucleotides of the compositions featured herein include dsRNAs, which comprise an RNA strand (the antisense strand) having a region which is less than 30 nucleotides in length, generally 18-30 nucleotides in length, specifically 21-23 nucleotides in length and is substantially complementary to at least part of an mRNA transcript of the target gene. In one embodiment the oligonucleotides are specifically between 18-30 nucleotides in length, encompassing those of 18, 19, 20, 21, 22, 23, 24, 25, 26, 27, 28, 29 or 30 nucleotides. The use of these dsRNAs enables the targeted degradation of mRNAs of genes that are implicated in replication and or maintenance of disease states, e.g. cancer, in mammals. Very low dosages of formulated dsRNAs with lipoproteins in particular can specifically and efficiently mediate RNAi, resulting in significant inhibition of expression of the target gene. The methods and compositions of the invention containing the formulated dsRNAs are useful for treating pathological processes mediated by target gene expression.

The pharmaceutical compositions featured in the invention include a dsRNA having an antisense strand comprising a region of complementarity which is less than 30 nucleotides in length, generally 18-30 nucleotides in length, and is substantially complementary to at least part of an RNA transcript of the target gene, optionally with a pharmaceutically acceptable carrier.

Lipoproteins

Lipoproteins are divided into four main classes: chylomicrons, which are particles that consist predominantly of triglycerides and which normally appear in larger quantities in plasma only after fatty meals, VLDL (Very Low Density Lipoproteins), LDL (Low Density Lipoproteins), and HDL (High Density Proteins). The nomenclature arises from the isolation of lipoproteins by means of ultracentrifugation. Classically, the lipoproteins are isolated in a density gradient. This method can only be applied on a laboratory scale as it requires a specialized apparatus and is very time-consuming. At best only a few hundred milligrams of lipoproteins or apolipoproteins can be produced using this method over a course of a few days. Other methods of isolating apolipoproteins or lipoproteins have also been known for some time; they are based in many cases on precipitation by means of divalent cations and/or polyethylene glycol or dextran, for example. A further possibility of isolating apolipoproteins is precipitation by means of alcohol fractionation, as described in patent EP 0 329 605 B1.

Reconstituted Lipoproteins

Methods of producing reconstituted lipoproteins have been described in scientific literature, especially for apolipoproteins A-1, A-II, A-IV, apoC and apoe (A. Jonas, Methods in Enzymology 128, 553-582 (1986)). The most frequent lipid used for reconstitution is phosphatidyl choline, extracted either from eggs or soybeans. Other phospholipids are also used, also lipids such as triglycerides or cholesterol. For reconstitution the lipids are first dissolved in an organic solvent, which is subsequently evaporated under nitrogen. In this method the lipid is bound in a thin film to a glass wall. Afterwards the apolipoproteins and a detergent, normally sodium cholate, are added and mixed. The added sodium cholate causes a dispersion of the lipid. After a suitable incubation period, the mixture is dialyzed against large quantities of buffer for a longer period of time; the sodium cholate is thereby removed for the most part, and at the same time lipids and apolipoproteins spontaneously form themselves into lipoproteins or so-called reconstituted lipoproteins. As alternatives to dialysis, hydrophobic adsorbents are available which can adsorb detergents (Bio-Beads SM-2, Bio Rad; Amberlite XAD-2, Rohm & Haas) (E. A. Bonomo, J. B. Swaney, J. Lipid Res., 29, 380-384 (1988)), or the detergent can be removed by means of gel chromatography (Sephadex G-25, Pharmacia). Lipoproteins can also be produced without detergents, for example through incubation of an aqueous suspension of a suitable lipid with apolipoproteins, the addition of lipid which was dissolved in an organic solvent, to apolipoproteins, with or without additional heating of this mixture, or through treatment of an apoA-1-lipid-mixture with ultrasound. With these methods, starting, for example, with apoA-I and phosphatidyl choline, disk-shaped particles can be obtained which correspond to lipoproteins in their nascent state. Normally, following the incubation, unbound apolipoproteins and free lipid are separated by means of centrifugation or gel chromatography in order to isolate the homogeneous, reconstituted lipoproteins particles. U.S. Pat. No. 5,128,318 describes a method of producing reconstituted HDL wherein phosphatidyl choline is dissolved in a solution with the aid of an organic solvent.

There are many disclosures of synthetic HDL-particles in the literature which refer to their capacity in picking up and removing undesired lipid material in the blood stream and from the blood vessels thus making them potentially useful in therapy for treating atherosclerosis by depleting cholesterol from arterial plaques and for removing lipid soluble toxins such as endotoxins.

In Experimental Lung Res. 1984, Vol. 6, pp. 255-270: A Jonas, experimental conditions of forming complexes of the partially hydrophobic apolipoproteins and phospholipids are described in detail. It was found that, by contacting apolipoproteins with preformed phosphatidyl choline vesicles, lipid particles were spontaneously formed which could be used as analogs of HDL-particles. By mixing phosphatidyl choline and bile acids to a miscellar dispersion and contacting the resultant mixture with apolipoproteins specifically shaped, discoidal and thermodynamically stable lipid particles were formed by means of a dialysis method, subsequently called the "cholate-dialysis method".

U.S. Pat. No. 4,643,988 to Research Corporation describes synthetic peptides useful in treatment of atherosclerosis with an improved amphiphatic helix and an ability to spontaneously form stable discoidal lipid particles with phospholipids which resemble native HDL-complexes. The lipid particles can be formed by contacting vesicles of phosphatidyl choline made by sonication. However, such a production method including sonication is suitable only for smaller batches of lipid particles and not for large scale pharmaceutical production.

U.S. Pat. No. 5,128,318 to Rogosin Institute describes the production of reconstituted lipoprotein containing particles (HDL-particles) from plasma derived apolipoproteins which are processed to synthetic particles for parenteral administration with the addition of cholate and egg yolk phosphatidyl choline. A similar method is also disclosed in the Japanese patent application JP 61-152632 to Daiichi Seiyaku KK.

Also in WO 87/02062 to Biotechn. Res. Partners LTD, it is disclosed how to obtain a stabilized formulation by incubating a solution of recombinantly produced lipid binding protein, such as human apolipoprotein, with a conventional lipid emulsion for parenteral nutrition.

The article by G. Franceschini et al. in J. Biol. Chem., 1985, Vol. 260 (30), pp. 16231-25 considers the spontaneous formation of lipid particles between apolipoprotein A-I and phosphatidyl choline. In this article, it is also revealed that Apo-IM (Milano), the variant of apolipoprotein A-I carried by individuals shown to have a very low prevalence of atherosclerosis, has a higher affinity (association rate) to dimyristoyl phosphatidyl choline (DMPC) than regular Apo A-1. It is suggested that the mutant Apo A-IM has a slightly higher exposure of hydrophobic residues which may contribute both an accelerated catabolism and an improved tissue lipid uptake capacity of such Apo A-IM/DMPC particles.

The Canadian patent application CA 2138925 to the Swiss Red Cross discloses an improved, more industrially applicable, method of producing synthetic reconstituted high density lipoprotein (rHDL) particles from purified serum apolipoproteins and phospholipids which avoids organic solvents while resulting in less unbound, free non-complexed phospholipids (i.e. a higher yield of lipoprotein particles). Herein, it is suggested to mix an aqueous solution of apolipoproteins with an aqueous solution of phospholipid and bile acids, whereupon the resultant mixture is incubated and protein-phospholipid particles are spontaneously formed when bile acids are removed from phospholipid/bile acid micelles with diafiltration.

Phospholipids which can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospholipids with defined fatty acid radicals, such as dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and combinations thereof, and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Phospholipids suitable for reconstitution with lipoproteins include, e.g., phosphatidylcholine, phosphatidylglycerol, lecithin, b, g-dipalmitoyl-a-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like.

Besides the amphiphilic agent, the lipid agent may comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 may be used in the present invention as well as acetylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agent can be added to the composition s in this invention, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable nonionic surfactants, include, but are not limited to various grades of Pluronic®, Poloxamer®, Span®, Tween®, Polysorbate®, Tyloxapol®, Emulphor® or Cremophor® and the like. The complementary surface active agents may also be of an ionic nature, such as bile duct agents, cholic acid or deoxycholic their salts and derivatives or free fatty acids, such as oleic acid, linoleic acid and others. Other ionic surface active agents are found among cationic lipids like C10-C24: alkylamines or alkanolamine and cationic cholesterol esters.

Also other pharmacologically acceptable components can be added to the lipid agent when desired, such as antioxidants (exemplified by alpha-tocopherol) and solubilization adjuvants (exemplified by benzylalcohol).

Oligonucleotides
Double-stranded Oligonucleotides

In one embodiment, the invention provides double-stranded ribonucleic acid (dsRNA) molecules for inhibiting the expression of the target gene (alone or incombinaton with a second dsRNA for inhibiting the expression of a second target gene) in a cell or mammal, wherein the dsRNA comprises an antisense strand comprising a region of complementarity which is complementary to at least a part of an mRNA formed in the expression of the target gene, and wherein the region of complementarity is less than 30 nucleotides in length, generally 19-24 nucleotides in length, and wherein said dsRNA, upon contact with a cell expressing said target gene, inhibits the expression of said target gene. The dsRNA comprises two RNA strands that are sufficiently complementary to hybridize to form a duplex structure. Generally, the duplex structure is between 15 and 30, more generally between 18 and 30, yet more generally between 19 and 24, and most generally between 19 and 21 base pairs in length. In certain embodiments, longer dsRNAs of between 18 and 30 base pairs in length are preferred. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the target gene is a human target gene.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above the dsRNAs of the invention can comprise at least one strand of a length of minimally 21 nucleotides. It can be reasonably expected that shorter dsRNAs comprising a known sequence minus only a few nucleotides on one or both ends may be similarly effective as compared to the dsRNAs of the lengths described above. Hence, dsRNAs comprising a partial sequence of at least 15, 16, 17, 18, 19, 20, or more contiguous nucleotides, and differing in their ability to inhibit the expression of the target gene in a FACS assay as described herein below by not more than 5, 10, 15, 20, 25, or 30% inhibition from a dsRNA comprising the full sequence, are contemplated by the invention. Further dsRNAs that cleave within the target sequence can readily be made using the target gene sequence and the target sequence provided.

The present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides coupled to additional nucleotide sequences taken from the region contiguous to the selected sequence in the target gene.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the target gene, the dsRNA generally does not contain any mismatch within the central 13 nucleotides. The methods described within the invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Preferred modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, an dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —$CH_2NHCH_2$—, —$CH_2N(CH_3)OCH_2$ [known as a methylene (methylimino) or MMI backbone], —$CH_2ON(CH_3)$—$CH_2$—, —$CH_2N(CH_3)N(CH_3)CH_2$— and —$N(CH_3)$—$CH_2$—$CH_2$— [wherein the native phosphodiester backbone is represented as —$OPOCH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred dsRNAs comprise one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxy-alkoxy group. A further preferred modification includes 2'-dimethylaminooxyethoxy, i.e., a O(CH2)2ON (CH3)2 group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-$OCH_2OCH_2N(CH_2)_2$, also described in examples hereinbelow.

Other preferred modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687, 808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, also herein incorporated by reference.

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Manoharan et al., Biorg. Med. Chem. Let., 1994 4 1053-1060), a thioether, e.g., beryl-S-tritylthiol (Manoharan et al., Ann. N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541, 313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

In some embodiments, an oligonucleotide described herein is covalently bound to a lipophilic ligand. Exemplary lipophilic ligands include cholesterol; bile acids; and fatty acids (e.g., lithocholic-oleyl acid, lauroyl acid, docosnyl acid, stearoyl acid, palmitoyl acid, myristoyl acid, oleoyl acid, or linoleoyl acid). The lipophilic ligand can be bound to the oligonucleotide directly or indirectly, for example, via a tether such as a tether that includes a cleavable linking group. In some embodiments, the lipophilic ligand is bound to the oligoneucleotide via a position on the oligonucleotide wherein a ribose of the oligonucleotide has been replaced, for example, by a monomer such as a pyrrolidine monomer.

Exemplary oligonucleotides covalently bound to a lipophilic moiety include the following structure of formula (I), incorporated into the oligonucleotide (e.g., an oligonucleotide described herein):

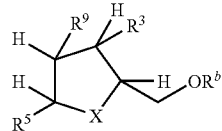
(I)

wherein:

X is N(CO)R$^7$, or NR$^7$;

each of R$^3$, R$^5$ and R$^9$, is, independently, H, OH, OR$^a$, OR$^b$;

R$^7$ is C$_1$-C$_{20}$ alkyl substituted with NRR$^d$ or NHC(O)R$^d$;

R$^a$ is:

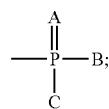

R$^b$ is

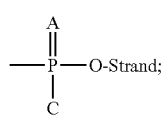

each of A and C is, independently, O or S;

B is OH, O$^-$, or

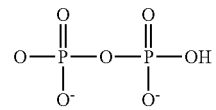

R$^C$ is H or C$_1$-C$_6$ alkyl; and

R$^d$ is a lipophilic ligand, including, for example, cholesterol; a bile acid; or a fatty acid (e.g., lithocholic-oleyl acid, lauroyl acid, docosnyl acid, stearoyl acid, palmitoyl acid, myristoyl acid, oleoyl acid, or linoleoyl acid). The lipophilic ligand, in some embodiments, can be furether tethered to a carbohydrate radical. Other exemplary monomers, which can be incorporated into an oligonucleotide described herein and covalently bound to a lipophilic moiety are described, for example, in US 2005/0107325, which is incorporated by reference herein in its entirety.

Single-stranded Oligonucleotides

Single stranded oliogonucleotides, including those described and/or identified as microRNAs or mirs which may be used as targets or may serve as a template for the design of oligonucleotides of the invention are taught in, for example, Esau, et al. US Publication 20050261218 (USSN: 10/909, 125) entitled "Oligomeric compounds and compositions for use in modulation small non-coding RNAs" the entire contents of which is incorporated herein by reference. It will be appreciated by one of skill in the art that any chemical modifications or variations which apply to the double stranded oligonucleotides described above, also apply to single stranded oligonucleotides. As such, said description has not been repeated here.

The stoichiometry of oligonucleotide to lipoprotein may be 1:1. Alternatively the stoichiometry may be 1:many, many: 1 or many:many, where many is greater than 2.

In one embodiment, the composition of the invention comprises lipoproteins to oligonucleotide in a ratio of at least 1:1, preferably about 1:3, preferably about 1:8, preferably about 1:10, preferably about 1:15, preferably about 1:20.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

The term "preassembled" is intended to encompass standard mixing of the agents of a composition. The term is also intended to embrace formation of complex between the agents of a composition. Complex can be via chemical interaction, such as, e.g., covalent, ionic, or secondary bonding (e.g., hydrogen bonding), and the like, or via physical interaction, such as, e.g., encapsulation, entrapment, and the like. The complex is formed prior to administration to a patient.

The phrase "RNA interference" and the term "RNAi" are synonymous and refer to the process by which a single, double, or tripartite molecule (e.g. an siRNA, an shRNA, an miRNA, a piRNA) exerts an effect on a biological process by interacting with one or more components of the RNAi pathway including but not limited to Drosha, RISC, Dicer, etc. The process includes, but is not limited to, gene silencing by degrading mRNA, attenuating translation, interactions with tRNA, rRNA, hnRNA, cDNA and genomic DNA, inhibition of as well as methylation of DNA with ancillary proteins. In addition, molecules that modulate RNAi (e.g. siRNA, piRNA, or miRNA inhibitors) are included in the list of molecules that enhance the RNAi pathway (Tomari, Y. et al. Genes Dev. 2005, 19(5):517-29).

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "target sequence" refers to a contiguous portion of the nucleotide sequence of an mRNA molecule formed during the transcription of the target gene, including mRNA that is a product of RNA processing of a primary transcription product. Target sequences may further include RNA precursors, either pri or pre-microRNA, or DNA which encodes the mRNA.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding target gene). For example, a polynucleotide is complementary to at least a part of a target gene mRNA if the sequence is substantially complementary to a non-interrupted portion of a mRNA encoding target gene.

As used herein the term "oligonucleotide" embraces both single and double stranded polynucleotides.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarilty is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to an oligonucleotide, means facilitating uptake or absorption into the cell, as is understood by those skilled in the art. Absorption or uptake of oligonucleotides can occur through unaided diffusive or active cellular processes, or by auxiliary agents or devices. The meaning of this term is not limited to cells in vitro; an oligonucleotide may also be "introduced into a cell", wherein the cell is part of a living organism. In such instance, introduction into the cell will include the delivery to the organism. For example, for in vivo delivery, oligonucleotides can be injected into a tissue site or administered systemically. In vitro introduction into a cell includes methods known in the art such as electroporation and lipofection.

The terms "silence" and "inhibit the expression of", in as far as they refer to target gene, herein refer to the at least partial suppression of the expression of the target gene, as manifested by a reduction of the amount of mRNA transcribed, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to the target gene transcription, e.g. the amount of protein encoded by the gene which is secreted by a cell, or the number of cells displaying a certain phenotype, e.g apoptosis. In principle, gene silencing may be determined in any cell expressing the target, either constitutively or by genomic engineering, and by any appropriate assay. However, when a reference is needed in order to determine whether a given oligonucleotide inhibits the expression of the gene by a certain degree and therefore is encompassed by the instant invention.

For example, in certain instances, expression of the gene is suppressed by at least about 20%, 25%, 35%, or 50% by administration of the compositions comprising the single- or double-stranded oligonucleotides of the invention when formulated with lipoproteins. In some embodiments, the target gene is suppressed by at least about 60%, 70%, or 80% by administration of the compositions comprising the oligonucleotides of the invention. In some embodiments, the target gene is suppressed by at least about 85%, 90%, or 95% by of the compositions comprising the oligonucleotides of the invention.

As used herein in the context of gene expression the terms "treat", "treatment", and the like, refer to relief from or alleviation of pathological processes mediated by target gene expression. In the context of the present invention insofar as it relates to any of the other conditions recited herein below (other than pathological processes mediated by target gene expression), the terms "treat", "treatment", and the like mean to relieve or alleviate at least one symptom associated with such condition, or to slow or reverse the progression of such condition, such as the slowing and progression of hepatic carcinoma.

As used herein, the phrases "therapeutically effective amount" and "prophylactically effective amount" refer to an amount that provides a therapeutic benefit in the treatment, prevention, or management of pathological processes mediated by target gene expression or an overt symptom of pathological processes mediated by target gene expression. The specific amount that is therapeutically effective can be readily determined by ordinary medical practitioner, and may vary depending on factors known in the art, such as, e.g. the type of pathological processes mediated by target gene expression, the patient's history and age, the stage of pathological processes mediated by target gene expression, and the administration of other anti-pathological processes mediated by target gene expression agents.

As used herein, a "pharmaceutical composition" comprises a pharmacologically effective amount of a oligonucleotide preassembled with lipoproteins and optionally a pharmaceutically acceptable carrier. As used herein, "pharmacologically effective amount," "therapeutically effective amount" or simply "effective amount" refers to that amount of an oligonucleotide preassembled with a lipoproteins effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical Compositions Comprising Formulated Oligonucleotides

In one embodiment, the invention provides pharmaceutical compositions comprising a oligonucleotide, as described herein, and a pharmaceutically acceptable carrier. The pharmaceutical composition comprising the oligonucleotide is useful for treating a disease or disorder associated with the expression or activity of the target gene, such as pathological processes mediated by target gene expression.

The pharmaceutical compositions featured herein are administered in dosages sufficient to inhibit expression of the target gene. In general, a suitable dose of total oligonucleotide will be in the range of 0.01 to 5.0 milligrams per kilogram body weight of the recipient per day, generally in the range of 1 microgram to 1 mg per kilogram body weight per day. The pharmaceutical composition may be administered once daily or may be administered as two, three, or more sub-doses at appropriate intervals throughout the day or even using continuous infusion or delivery through a controlled release formulation. In that case, the oligonucleotide contained in each sub-dose must be correspondingly smaller in order to achieve the total daily dosage. The dosage unit can also be compounded for delivery over several days, e.g., using a conventional sustained release formulation which provides sustained release of the oligonucleotide over a several day period. Sustained release formulations are well known in the art and are particularly useful for delivery of agents at a particular site, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo halflives for the individual oligonucleotides encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by target gene expression. Such models are used for in vivo testing of oligonucleotide, as well as for determining a therapeutically effective dose.

The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the compositions of the invention are in admixture with a topical delivery agent such as lipids, liposomes, fatty acids, fatty acid esters, steroids, chelating agents and surfactants.

Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compositions of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. DsRNAs of the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application. Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Additional compositions useful for parenteral, intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the lung, muscle and heart.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions of the present invention may be prepared and formulated as emulsions. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems can be used in the delivery of drugs to the skin, in particular systems comprising non-ionic surfactant and cholesterol. Non-ionic liposomal formulations comprising Novasome™ I (glyceryl dilaurate/cholesterol/po-lyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes of the compositions also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the compositions of the present invention employs various penetration enhancers to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Carriers

Certain compositions of the present invention may also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more oligonucleotide compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pathological processes mediated by target gene expression. In any event, the administering physician can adjust the amount and timing of oligonucleotide administration on the basis of results observed using standard measures of efficacy known in the art or described herein.

Methods for Treating Diseases Caused by Expression of a Target Gene Using the Compositions of the Invention The invention relates in particular compositions comprising (a) at least one of a single or double stranded oligonucleotide, where said oligonucleotide has been conjugated to a lipophile to which the conjugated oligonucleotide has been preassembled with a lipoproteins for the treatment of a disease. In one embodiment, the described compositions can be used in combination with other known treatments to treat conditions or diseases. For example, the described compositions can be used in combination with one or more known therapeutic agents to treat breast, lung, prostate, colorectal, brain, esophageal, bladder, pancreatic, cervical, head and neck, and ovarian cancer, melanoma, lymphoma, glioma, multidrug resistant cancers, and/or HIV, HBV, HCV, CMV, RSV, HSV, poliovirus, influenza, rhinovirus, west nile virus, Ebola virus, foot and mouth virus, papilloma virus, and SARS virus infection, other cancers and other infectious diseases, autoimmunity, inflammation, endocrine disorders, renal disease, pulmonary disease, cardiovascular disease, CNS injury, CNS disease, neurodegenerative disease, birth defects, aging, any other disease or condition related to gene expression.

The invention furthermore relates to the use of present composition thereof, e.g., for treating cancer or for preventing tumor metastasis, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluorouracil, adriamycin, daunorubicin or tamoxifen.

The invention can also be practiced by including with a specific oligonucleotide, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

Methods for Inhibiting Expression of the Target Gene Using the Composition of the Present Invention In yet another aspect, the invention provides a method for inhibiting the expression of the target gene in a mammal. The method includes administering a composition featured in the invention to the mammal such that expression of the target gene is silenced.

In one embodiment, a method for inhibiting target gene expression includes administering a composition containing a nucleotide sequence that is complementary to at least a part of an RNA transcript of the target gene and the other having a nucleotide sequence that is complementary to at least a part of an RNA transcript of the gene of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Detailed experiments and results were presented in Wolfrum, et al., *Nature Biotechnology* 25, 1149-1157 (2007), which is herein incorporated by reference in its entirety.
Oligonucleotide Synthesis
Source of Reagents Where the source of a reagent is not specifically given herein, such reagent may be obtained from any supplier of reagents for molecular biology at a quality/purity standard for application in molecular biology.
siRNA (dsRNA) Synthesis Single-stranded RNAs were produced by solid phase synthesis on a scale of 1 pmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, UnterschleiBheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:
Diethyl-2-azabutane-1,4-dicarboxylate AA

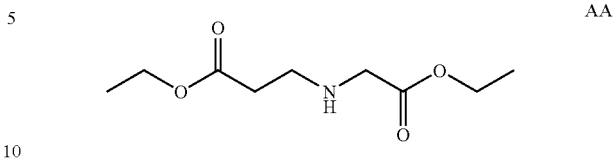

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

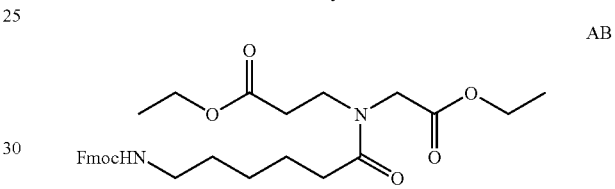

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

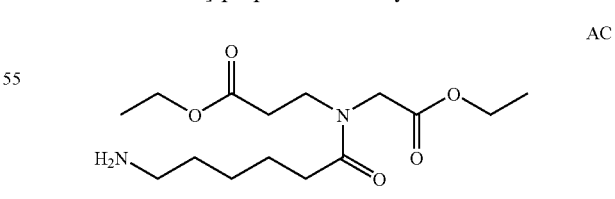

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

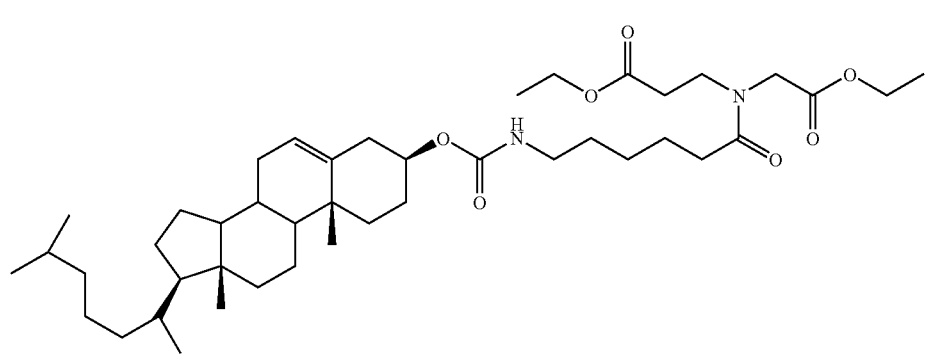

AD

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

1-{6-[17-(1,5-Dimethyl-hexyl)-10,13-dimethyl-2,3,4,7,8,9,10,11,12,13,14,15,16,17-tetradecahydro-1H-cyclopenta[a] phenanthren-3-yloxycarbonylamino]-hexanoyl}-4-oxo-pyrrolidine-3-carboxylic acid ethyl ester AE

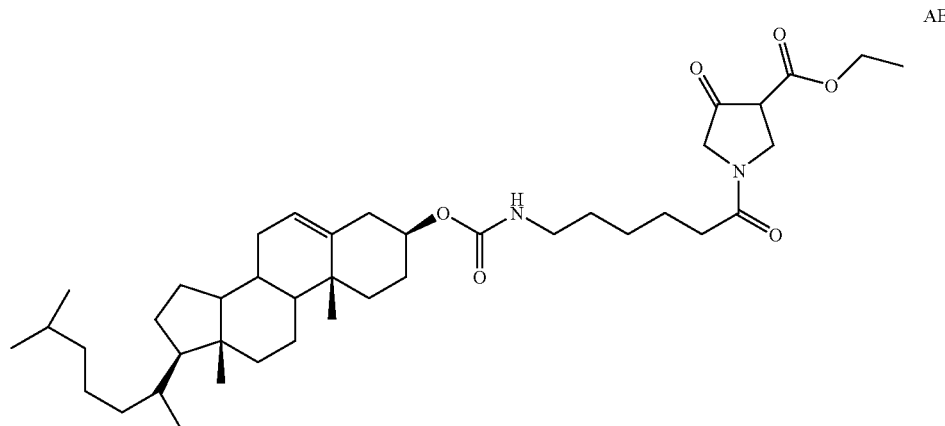

AE

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

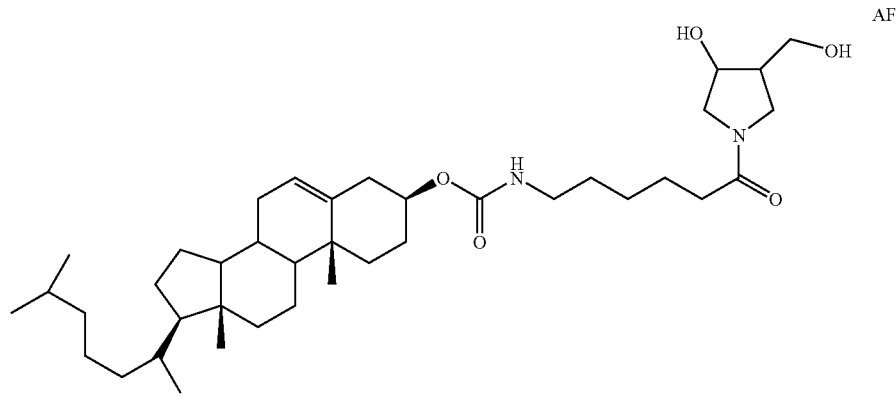

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

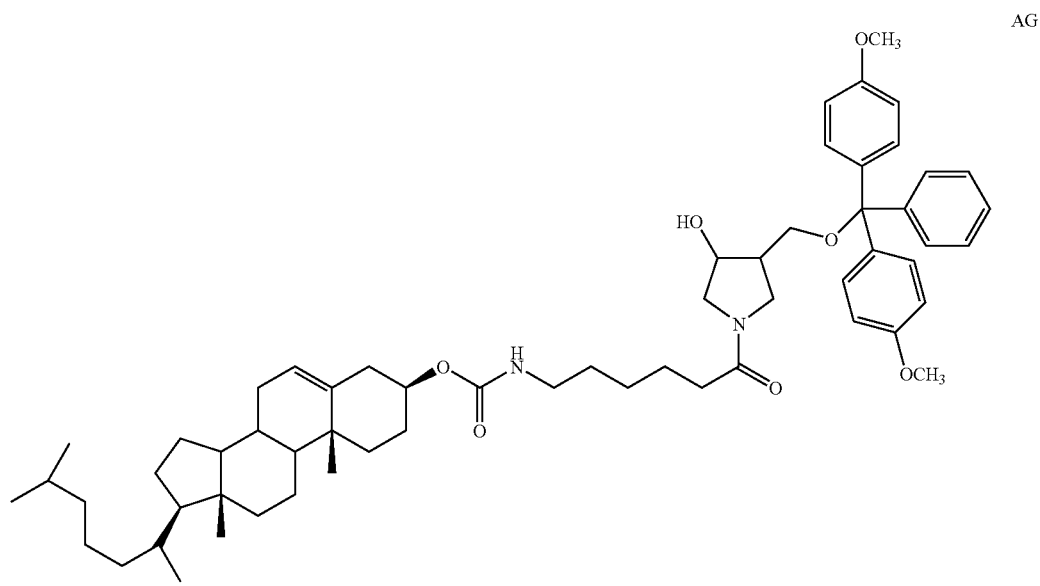

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

AH

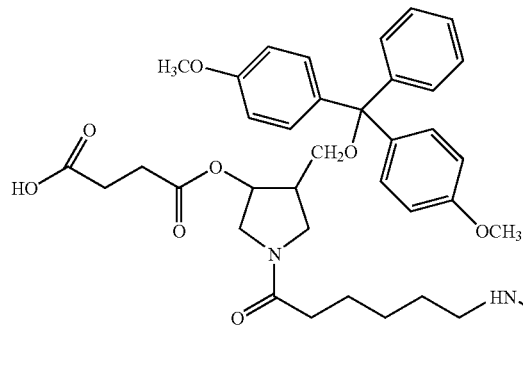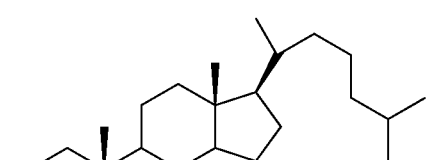

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol derivatised CPG AI added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented using standard nomenclature, and specifically the abbreviations of Table 1.

AI

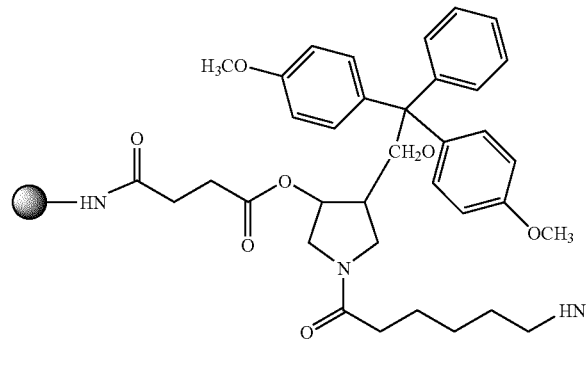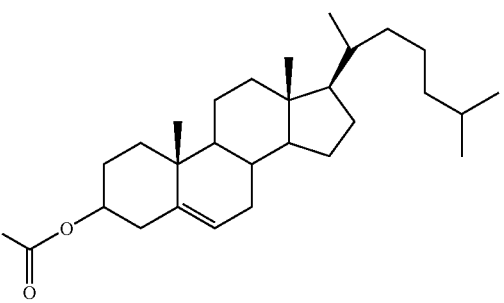

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was

TABLE 1

Abbreviations of nucleotide monomers used in nucleic acid sequence representation.

| Abbreviation | Nucleotide(s) |
|---|---|
| A | adenosine-5'-phosphate |
| C | cytidine-5'-phosphate |
| G | guanosine-5'-phosphate |
| T | 2'-deoxy-thymidine-5'-phosphate |
| U | uridine-5'-phosphate |

TABLE 1-continued

Abbreviations of nucleotide monomers used
in nucleic acid sequence representation.

| Abbreviation | Nucleotide(s) |
| --- | --- |
| N | any nucleotide (G, A, C, or T) |
| s or subscript 's' | Phosphorothioate linkage |
| sT | 2'-deoxy-thymidine-5'phosphate-phosphorothioate |
| L | the lipophile |
| Chol | Cholesterol |
| P | phosphate group |
| fC | 2'-deoxy-2'-fluoro cytidine |
| fU | 2'-deoxy-2'-fluoro uridine |
| u, c, g, a | lower case letters, 2'-O-methyl sugar modification |

It will be understood that these monomers, when present in an oligonucleotide, are mutually linked by 5'-3'-phosphodiester bonds.

Synthesis of Sequences of Lipophile-conjugated si-RNAs,

The chemically modified, lipophile-conjugated siRNA-apoB1 constituted from the corresponding sense strand: 5'-GUCAUCACACUGAAUACCAAU$_s$Hyp-L-3' (SEQ ID NO:1) and antisense strand: 5'-AUUGGUAUUCAGU-GUGAUGAc$_s$a$_s$C-3' (SEQ ID NO:2) was obtained. The cholesterol-siRNA-apoM was prepared from cholesterol-conjugated sense strand: 5'-AsGsfUfCAAfUfCGGfUAfUGfUfC fCAfC$_s$dT$_s$dT$_s$-cholesterol-3' (SEQ ID NO:3) and 5'-phosphorylated antisense strand: 5'-P-GsfUGGAfCAfUAfCfC-GAfUfUGAfCfU$_s$dT$_s$dT, (SEQ ID NO:4) where all pyrimidines except overhangs were substituted with corresponding 2'-deoxy-2'-fluoro nucleosides. The corresponding mismatched cholesterol-mm-siRNA-apoM was constituted sense strand: 5'-AsGsfUfCAGfUfCAGfUGfUAfUfCf-CAfCsdTsdTs-cholesterol-3' (SEQ ID NO:5) and 5'-phosphorylated antisense strand: 5'-P-GsfUG GAfU AfCA fCfUG AfCfU GAfC fUsdTsdT-3'(SEQ ID NO:6). Abbreviations are as follows: L, the lipophile; P, phosphate group; fC and fU, 2'-deoxy-2'-fluoro cytidine and uridine respectively; lower case letters, 2'-O-methyl sugar modification; subscript 's', phosphorothioate linkages.

Sense and antisense strands of control and corresponding 3'-lipophile conjugated sense strands were individually synthesized and purified according to the standard oligonucleotide synthesis and deprotection protocols. Commercially available 5'-O-(4,4'-dimethoxytrityl)-2'-O-t-butyldimethylsilyl-3'-O-(2-cyanoethyl-N,N-diisopropyl) RNA and the corresponding 2'-O-methyl phosphoramidite monomers of 6-N-benzoyladenosine (A Bz), 4-N-acetylcytidine (CAC), 2-N-isobutyrylguanosine ($G^{iBu}$), and uridine (U) were used for unmodified and 2'-O-methyl sugar modified RNA synthesis. The 2'-deoxy-2'-fluoro sugar modified pyrimidines were introduced to the RNA by using 5'-O-(4,4'-dimethoxytrityl)-2'-deoxy-2'-fluoro-3'-O-(2-cyanoethyl-N,N-diisopropyl) phosphoramidite monomers of 4-N-acetylcytidine (CAC) and uridine (U).

Each individual lipophile-conjugated sense strand was synthesized from the corresponding hydroxyprolinol-lipophile solid support. Lipophile was tethered to trans-4-hydroxyprolinol via a 6-aminohexanoate linkage to obtain a hydroxyprolinol-lipophile moiety that was subsequently attached to a functionalized control pore glass to obtain the solid support. Beaucage reagent was used as an oxidant to obtain the phosphorothioate backbone modification. The lipophile-conjugated sense strands were purified by reversed phase-high-performance liquid chromatography (RP-HPLC) on an in-house packed Source 15RPC resin reversed-phase column. The buffers were 20 mM sodium acetate in 10% $CH_3CN$ (buffer A) and 20 mM sodium acetate in 70% $CH_3CN$ (buffer B). The unconjugated RNA oligonucleotides were purified by anion-exchange HPLC. Fractions containing full-length oligonucleotides were pooled, desalted and lyophilized. Analytical HPLC, capillary gel electrophoresis and electrospray liquid chromatography-mass spectrometry established the integrity of the compounds. For duplex generation, equimolar amounts of sense and antisense strand were heated in 1×PBS at 95° C. for 5 min and slowly cooled to 20° C. Annealing of equimolar mixture of sense and antisense strands in 1×PBS buffer afforded the desired siRNA.

Radiolabeling of siRNAs and Lipoproteins.

Different siRNAs were labeled using T4 polynucleotide kinase (New England Biolabs) and $\gamma^{32}$P-ATP. Unbound nucleotides were separated by gel filtration using G50 spin columns. Lipoproteins were isolated by FPLC (Amersham) and dialyzed twice against 2 liters of reaction buffer (1 M glycine pH 9.5, 100 mM NaCl). Lipoprotein-containing fractions were concentrated using Centripreps (10-kDa cutoff) to 10 mg/ml protein. Lipoproteins were labeled indirectly with tyramine cellobiose using freshly prepared [$^{125}$I]Cl solution. Unbound free iodine or iodine-labeled tracer was separated by PD-10 columns (Pharmacia).

Annealing of siRNA to Lipoproteins and Albumin.

Lipoproteins from hamster or mouse were isolated by ultracentrifugation. Labeled or unlabeled siRNAs were annealed with lipoproteins or albumin at a 4-M siRNA excess at 20° C. for 30 min, unbound siRNAs were separated from the complex by gel filtration using a Suprose6 column (Pharmacia). To assess binding constants and ratios for cholesterol-siRNA binding to albumin or lipoprotein particles, we incubated known amounts of cholesterol-siRNA with either binding partner. After annealing, bound and unbound fractions were separated and quantified. The binding constant was calculated from the ratio of bound versus unbound cholesterol-siRNA.

Injection of siRNA.

Mice were injected with saline or different lipophile-siRNA conjugates through the tail vein, whereas hamsters were injected through the saphenous vein. For in vivo silencing, the apoB siRNA, cholesterol-siRNA-apoBI was administered at a dose of 50 mg kg$^{-1}$ at a dosing volume of 10 μl/g. For uptake and transport studies, animals were injected with ~0.5-2 mg kg$^{-1}$ of $^{32}$P labeled siRNA bound to lipoproteins/albumin or in a free form. Animals were killed at different time points and blood and tissue was taken for RNA analysis or to measure uptake of radiolabeled siRNAs. Circulating cholesterol-siRNA concentration was calculated from the specific activity of the radiolabeled compounds.

Cell Lines and siRNA Transfection.

HepG2 cells were maintained in DMEM supplemented with 4.5 g/l glucose, 10% FCS, 2 mM glutamine; 50 μg/ml gentamycin/streptomycin in a humidified incubator at 5% $CO_2$. Cells were grown on collagen-treated plates and transfected with siRNAs using the Mirus transfection reagent (Mirus). For knockdown of human Sid1 (NM_017699) either Sid no. 1 siRNA (5'-GCAGCAACTGATATTTGTA) (SEQ ID NO:7) or Sid no. 2 siRNA (5'-AGCTGGTCATTAC-CTATCA) (SEQ ID NO:8)were used.

Liver Perfusion.

After anesthesia with pentobarbitone sodium (60 mg/kg intraperitoneally), the portal vein and the inferior vena cava were cannulated. The liver was perfused with oxygenated Krebs-Henseleit buffer with varying amounts of lipoproteins and cholesterol-siRNAs at 37° C. in a single-pass mode with a total flow rate of 1.5-2 ml/min.

ApoB mRNA Cleavage Assay.

Total RNA (5 μg) from liver and cells was ligated to an adaptor primer without prior treatment. Ligated RNA was reverse-transcribed using a gene-specific primer (5'-CTCCT-GTTGCAGTAGAGTGCAGCT-3') (SEQ ID NO:9) (Ambion). To detect cleavage products a radiolabeled, we performed PCR using primers complementary to the RNA adaptor (GR5': 5'-CTCTAGAGCGACTGGAGCACGAG-GACACTA-3') (SEQ ID NO:10) and apoB mRNA (Rev2: 5'-ACGCGTCGACGTGGGAGCATGGAGGTTG-GCAGTTGTTC-3'). (SEQ ID NO:11)Products were resolved by gel electrophoresis and visualized by autoradiography. Band intensity was quantified using the LabImage software.

Quantitative RT-PCR.

The QuantiGene assay (Genospectra) was used to quantify the reduction of apoB mRNA in liver after siRNA treatment. Small uniform tissue samples were collected 24 h after the last injection. Lysates from three tissue samples per animal were directly used for apoB and GAPDH mRNA quantification, and the ratio of apoB and GAPDH mRNA was calculated and expressed as a group average relative to the saline control group. Specific probes for detection of apoB mRNA levels have been described earlier.

Figure 2:
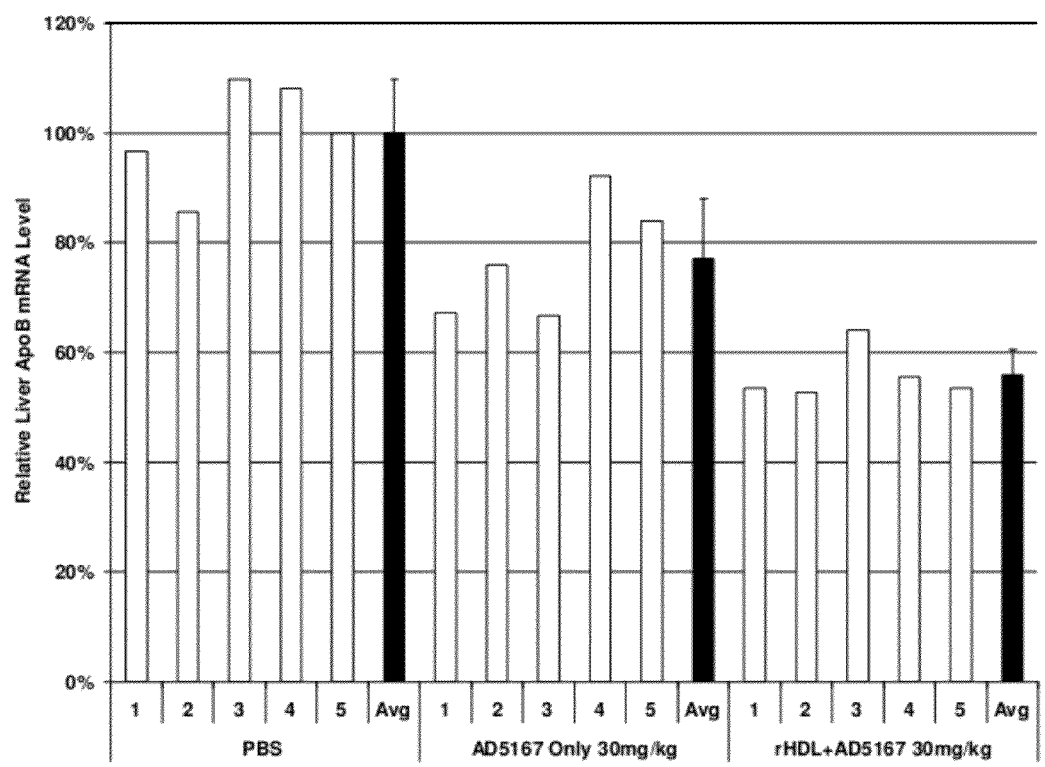
FIG. 2 shows that pre-mixing of AD5167 with rHDL results in ~45% silencing of ApoB; Groups: PBS, rHDL-AD5167 @ 30 mg/kg, AD5167 @ 30 mg/kg; y axis is relative liver Apo B mRNS level.
Figure 3:
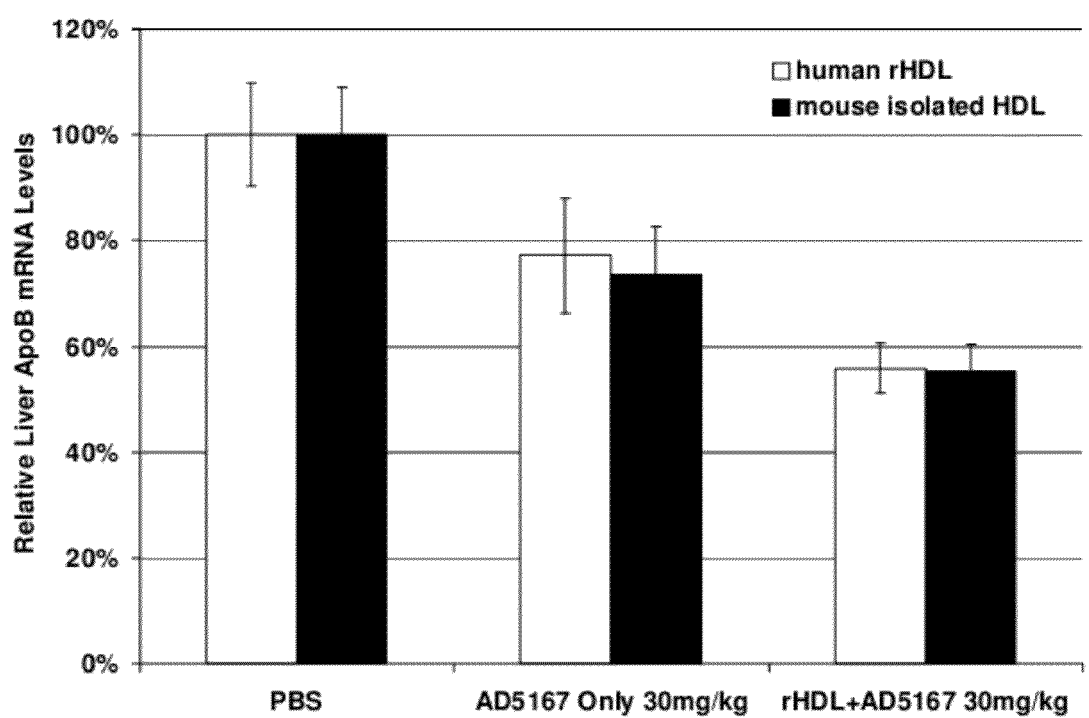
FIG. 3 illustrates the difference between human rHDL and mouse isolated HDL; identical results were obtained; Groups: PBS, rHDL-AD5167 @ 30 mg/kg, AD5167 @ 30 mg/kg; y axis is relative liver Apo B mRNS level.

Preparation of Reconstituted HDL (rHDL)
Composition:
Human ApoAl, Lee Biosciences (10 mg)
POPC, Avanti Polar Lipids (25 mg)
Cholesterol, Sigma-Aldrich (1.3 mg)
Well-established sodium cholate dialysis method used (Matz & Jonas, JBC, 1981.)
PC, Chol, and ApoA1 mixed in the presences of sodium cholate (detergent)
Cholate removed by dialysis to form rHDL
Final concentrations of ApoAl, POPC, and cholesterol determined by routine assays
rHDL appear only slightly larger than isolated mouse HDL by SEC HPCL (see FIG. 1).
In vivo efficacy of AD-5167 and AD5544
Methods
Preparation of rHDL-AD5167 mixture
rHDL:AD5167=1:3 (mol:mol)
rHDL and AD5167 mixed and incubated at room temperature for 1 h
Final concentration=3 mg/mL (siRNA)
In vivo protocol
C57BL6 mice, female (5 per group)
Groups: PBS, rHDL-AD5167 @ 30 mg/kg, AD5167 @ 30 mg/kg
Single i.v. bolus administration
Livers harvested for bDNA analysis 48 h post-administration As shown in FIG. 2, pre-mixing AD-5167 with rHDL results in 45% silencing of ApoB when compared with PBS and AD5167 alone. Identical results were obtained with human rHDL as with mouse isolated HDL (FIG. 3).

Figure 4:
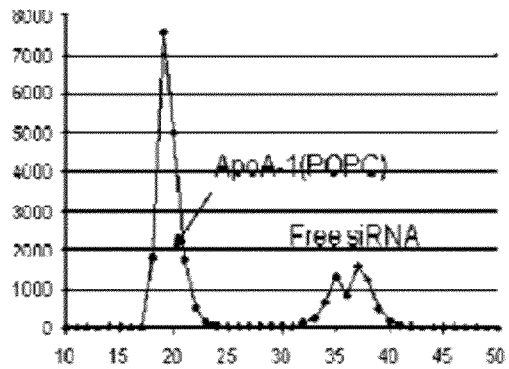
FIG. 4 depicts FPLC elution profiles of reconstituted lipoprotein particles complexed with AD5167 and AD5544; (a) ApoA1(POPPC) with AD5167; (b) ApoE(DPPC) with AD5167; (c) ApoA1(POPC) with AD5544; (d) ApoE(DPPC) with AD5544; y axis represents cpm and x axis represents fraction.
Figure 4:
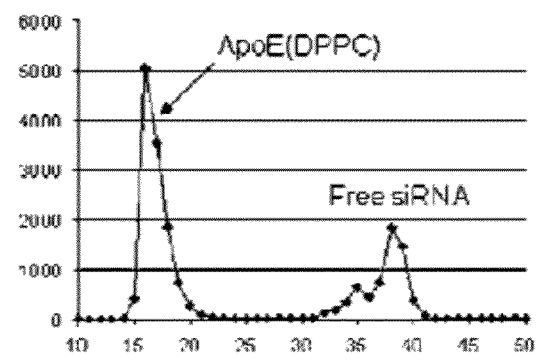
Figure 4:
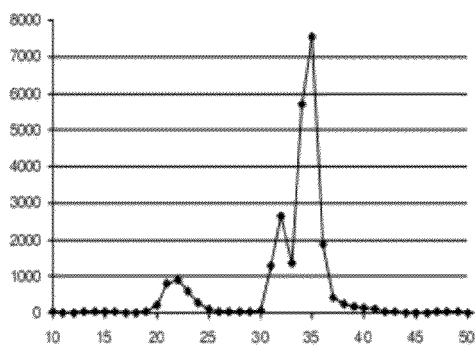
Figure 4:
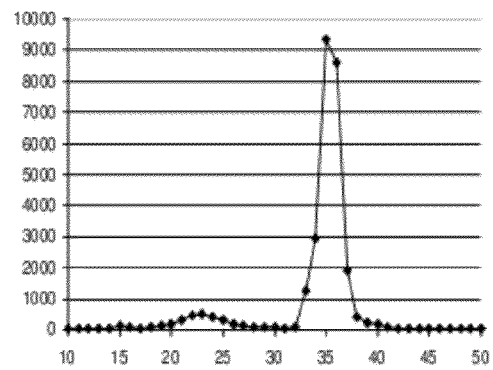
Figure 5:
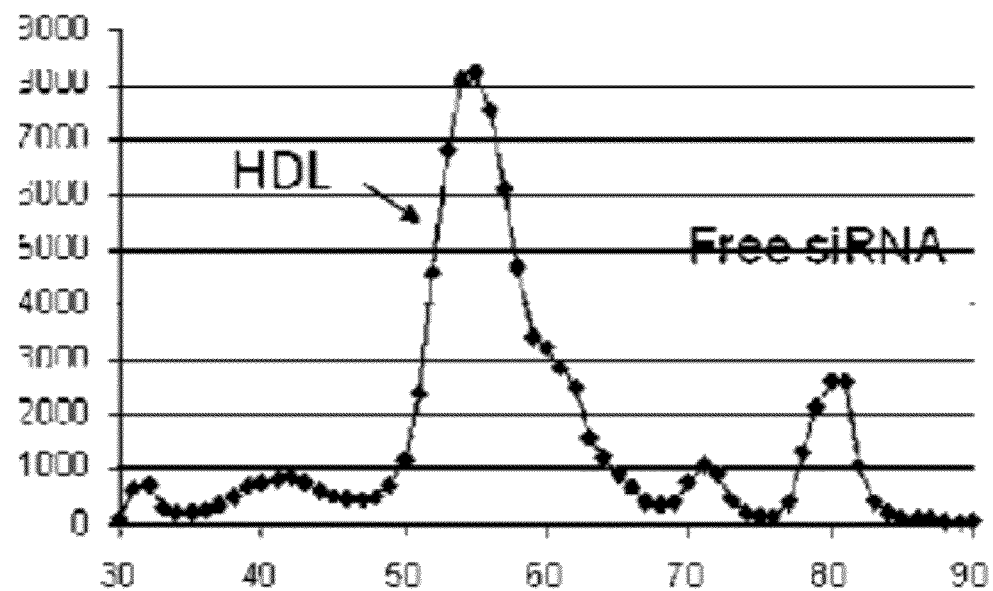
FIG. 5 illustrates siRNA binding to HDL in mouse plasma: (a) AD5167; (b) AD5544; y axis represents cpm and x axis represents fraction.
Figure 5:
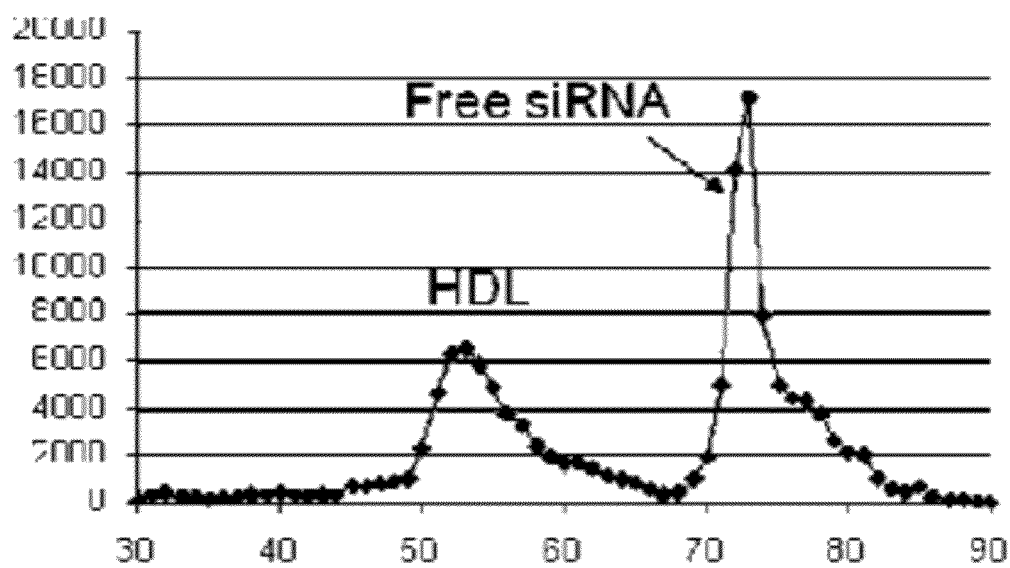
Figure 6:
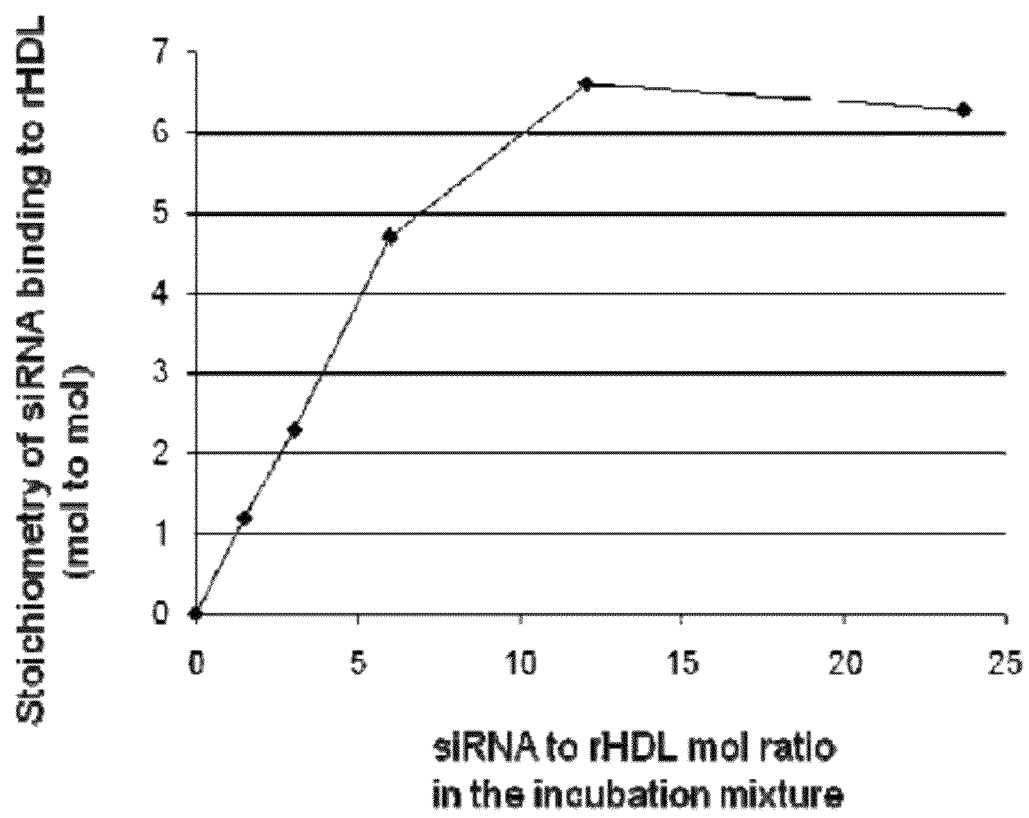
FIG. 6 represents a titration curve of reconstituted lipoprotein particles (ApoA-1, POPC) with AD5167; y axis represents stoichiometry of siRNA binding to rHDL (mol to mol) and x axis represents siRNA to rHDL mol ratio in the incubation mixture.

Lipoprotein Binding Assay Methods
Loading reconstituted lipoprotein particles with siRNA
$^{32}$P-labeled AD5167 and AD5544 incubated with reconstituted particles at
a molar ratio of 8:1 (siRNA:particle)
Quantitation of siRNA bound to reconstituted lipoprotein particles
Fractionation of incubation mixtures by gel-filtration FPLC
Determination of the amount of siRNA bound to the lipoprotein particles from the radioactivity in lipoprotein particle-containing fractions FIG. 4 illustrates the FPLC elution profiles of reconstituted lipoprotein particles complex with AD5167 and AD5544. Suprose 6 column was used fro apoE(DPPC) with AD5544 and Superdex 200 column was used for all others. FIG. 5 represents siRNA binding to HDL in mouse plasma. 82% of $^{32}$P of AD5167 siRNA is in the HDL-containing fractions, while 50% of $^{32}$P of AD5544 is in the HDL-containing fractions.

siRNA binding assay
$^{32}$ P-labeled siRNAs were prepared by treating a sense or anti-sense strand with T4 kinase and gamma $^{32}$P-ATP and annealing with their corresponding cholesterol conjugated anti-sense or sense strand. Reconstituted lipoprotein particles were incubated with $^{32}$P-siRNA (1 to 32 nmol) in the total of 150 ul reaction volume for 1 h at RT. Reconstituted lipoprotein particle and free siRNA were separated by gel filtration FPLC (Superose 6 10/300) using PBS as the elution buffer. The amount of siRNA bound to the reconstituted lipoprotein particle was calculated from the radioactivity eluted with the lipoprotein particle. FIG. 6 illustrates the titration curve of reconstituted lipoprotein particle (apoA-1, POPC) with AD5167.

TABLE 1

| AD5167 and AD5644 Duplex | | |
|---|---|---|
| AD5167 | (S) | 5'-GUCAUCACACUGAAUACCAAUsChol-3' (SEQ ID NO: 1) |
|  | (AS) | AUUGGUAUUCAGUGUGAUGAoCsoAsC (SEQ ID NO: 2) |
| AD5544 | (S) | 5'-GGAAUCuuAuAuuuGAUCcAAsChol-3' (SEQ ID NO: 12) |
|  | (AS) | uuGGAUcAAAuAuAAGAuUCcscsU (SEQ ID NO: 13) |

TABLE 2

Molar ratio of siRNA binding to reconstituted lipoprotein particles (when incubated with 8-fold molar excess of siRNA)

|  | ApoA-1 (POPC) | ApoE (DPPC) |
|---|---|---|
| AD5167 | 5.9 | 5.7 |
| AD5544 | 0.47 | 0.48 |

Very little AD5544 binds apoA-1(POPC) and apoE(DPPC) particles, but surprisingly 6 molecules of AD5167 bind one molecule of each particle when incubated at a 1:8 molar ratio.
A greater than 1:6 stoichiometry of binding is likely if incubated with a higher concentration of AD5167.
The results indicate siRNA chemical modification and/or sequence greatly affects binding of siRNA to reconstituted lipoproteins.
Previous study with mouse plasma hinted that the incorporation of AD5167 to (mature) HDL is higher than AD5544 (FIG. 5). This may be one reason why AD5167 is more efficacious in vivo.

The invention claimed is:

1. A composition comprising
   (a) at least one oligonucleotide and
   (b) at least one lipoprotein, wherein the lipoprotein comprises a reconstituted lipoprotein, wherein the at least one oligonucleotide and the at least one lipoprotein are preassembled, and
      wherein the reconsititued lipoprotein is a reconstituted high density lipoprotein (rHDL) selected from the group consisting of apoA-1, apoA-II, apoA-IV, apoC and apoE.

2. The composition of claim 1, wherein the at least one oligonucleotide is conjugated to a lipophile.

3. The composition of claim 1, wherein the at least one oligonucleotide comprises a double stranded oligonucleotide.

4. The composition of claim 1, wherein the lipoprotein is reconstituted with at least one amphiphilic agent.

5. The composition of claim 4 wherein the amphiphilic agent is a phospholipid.

6. The composition of claim 5 wherein the phospholipid is selected from the group consisting of dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and combinations thereof.

7. The composition of claim 1 wherein the ratio of lipoprotein to oligonucleotide is at least about 1:1.

8. The composition of claim 1 wherein the ratio of lipoprotein to oligonucleotide is about 1:3.

9. The composition of claim 1 wherein the ratio of lipoprotein to oligonucleotide is about 1:8.

10. The composition of claim 1 wherein the ratio of lipoprotein to oligonucleotide is about 1:10.

11. The composition of claim 1 wherein the ratio of lipoprotein to oligonucleotide is about 1:15.

12. The composition of claim 1 wherein the ratio of lipoprotein to oligonucleotide is about 1:20.

13. The composition of claim 3, wherein said double stranded oligonucleotide comprises a sense strand and an antisense strand, wherein each of said strands comprises 18 to 30 nucleotides and said strands form a complementary double stranded region of 18 to 30 basepairs.

14. The composition of claim 13, wherein said complementary double stranded region has 0, 1, 2, or 3 nucleotide single stranded overhangs on at least one terminal end.

15. The composition of claim 1, wherein the at least one oligonucleotide comprises at least one non-phosphodiester linkage.

16. The composition of claim 1, wherein the at least one oligonucleotide comprises at least one modified nucleoside.

17. The composition of claim 1 wherein the lipoprotein comprises a cholesterol moiety.

18. The composition of claim 1 wherein the at least one oligonucleotide is single stranded.

* * * * *